(12) United States Patent
Bloodsaw

(10) Patent No.: US 6,418,931 B1
(45) Date of Patent: Jul. 16, 2002

(54) ORAL CONDOMS WITH DETACHABLE FASTENERS

(76) Inventor: Paula A. Bloodsaw, 302 SW. 85th way, #307, Pembrook Pines, FL (US) 33025

( * ) Notice: Subject to any disclaimer, the term of this patent is extended or adjusted under 35 U.S.C. 154(b) by 0 days.

(21) Appl. No.: 09/864,039

(22) Filed: May 22, 2001

(51) Int. Cl.[7] .................................................. A61F 6/02
(52) U.S. Cl. ........................ 128/842; 128/844; 128/918; 128/857; 2/15
(58) Field of Search ................................. 128/846, 848, 128/857–862, 206.21; 2/2, 15, 410

(56) References Cited

U.S. PATENT DOCUMENTS

| | | | |
|---|---|---|---|
| 4,974,605 A | * 12/1990 | Esqueda | ...................... 128/857 |
| 5,320,112 A | 6/1994 | Bloodsaw | |
| 5,409,016 A | 4/1995 | Bloodsaw | |
| 5,449,486 A | * 9/1995 | Hopkins | ...................... 128/859 |
| 5,655,543 A | * 8/1997 | Bloodsaw | ...................... 128/842 |

* cited by examiner

Primary Examiner—Michael A. Brown
(74) Attorney, Agent, or Firm—Thomas I. Rozsa; Tony D. Chen

(57) ABSTRACT

An apparatus for protecting the user from contracting sexually transmitted diseases while engaging in cunnilingus and anal sex. The apparatus includes an oral condom mask and two opposite detachable adjustable fasteners. The detachable adjustable fasteners facilitate the fastening and releasing of the lateral portions of the oral condom mask. Each fastener includes a springy middle section between a front hook section and a rear ear engagement section for adjusting the length of the fastener so that any particular user can use the fasteners. A cylindrical locking sleeve is slidable installed on the fastener to secure the lateral end of the oral condom mask.

17 Claims, 3 Drawing Sheets

ORAL CONDOMS WITH DETACHABLE FASTENERS

BACKGROUND OF THE INVENTION

1. Field of the Invention

The present invention relates generally to the field of protective masks. More particularly, the present invention relates to the field of oral condom masks with detachable fasteners.

2. Description of the Prior Art

The inventor and applicant of the present invention is also the patentee of U.S. Pat. No. 5,320,112 issued on Jun. 14, 1994 (hereafter "the '112 Patent") and U.S. Pat. No. 5,409,016 issued on Apr. 25, 1995 (hereafter "the '016 Patent"). The inventor is aware of the prior art references which were disclosed in the '112 and '016 Patents. While the patentee's devices disclosed in the '112 and '016 Patents function adequately, the patentee has continuously sought to further improve her detachable fasteners used in conjunction with an oral condom mask.

Both the '112 and '016 Patents disclose an oral condom mask which protects the user from contracting sexually transmitted diseases while engaging in sexual activities. The oral condom mask provides protection to the facial area of a user from undesirable exposure to infection carrying microorganisms. The oral condom mask has conformed portions for the lips so that the user's lips can be easily moved in a natural way and a protruding portion for the tongue so that the user's tongue can be easily moved in a natural way and not be hindered by the mask.

In the '112 Patent, the oral condom mask is shaped like an oval with two lateral leg portions which are respectively attached to two unique opposite ear attachments. In the '016 Patent, the oral condom mask is a unitary piece integrally formed with the ear attachments.

There is always a need to improve the ear attachments for protective masks, so that a user engaging in sexual activities will be protected from communicable diseases. Therefore, it is highly desirable to have a very efficient and also very effective design and construction of a detachable adjustable fastener to be used with an oral condom mask, to thereby facilitate the effective use of the mask. It is desirable to provide a detachable adjustable fastener with the capability of rapidly securing the ends of the oral condom mask, which can also be quickly released when required. It is also desirable to provide a detachable adjustable fastener that is flexible enough to allow repositioning the ear portion of the detachable fastener for a particular user to provide optimum use of the condom mask in a much more efficient way.

SUMMARY OF THE INVENTION

The present invention is an apparatus for protecting the user from contracting sexually transmitted diseases while engaging in sexual activities. The apparatus includes an oral condom mask and two opposite detachable adjustable fasteners. The detachable adjustable fasteners facilitate the fastening and releasing of the lateral portions of the oral condom mask.

It is an object of the present invention to provide detachable adjustable fasteners which can be used in conjunction with an oral condom mask to facilitate the fastening and releasing of the oral condom mask.

It is also an object of the present invention to provide detachable adjustable fasteners which include a springy middle section between a front hook portion and a rear ear engagement portion for adjusting the length of the fastener so that any particular user can use the detachable adjustable fasteners in a much more efficient way. The special feature of the springy middle section makes it particularly useful when material used for the membrane is made of plastic materials or a derivative thereof. Plastic materials do not provide the elasticity to permit adjustable lengths, whereas this special feature will provide adjustable lengths for any particular user.

It is an additional object of the present invention to provide detachable adjustable fasteners including a cylindrical locking sleeve which is slidable on the fastener to secure the lateral end of the oral condom mask.

It is a further object of the present invention to provide detachable adjustable fasteners which are used in conjunction with an oral condom mask, so that the tension on the oral condom mask against the user's face can easily be adjusted.

It is still a further object of the present invention to provide detachable adjustable fasteners which are efficient and easy to use with an oral condom mask and which are disposable after use so that when in use, the detachable adjustable fasteners can be easily and removably clamped to the oral condom mask and then the fasteners can be reused with another oral condom mask.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Describe briefly, the present invention is an apparatus for preventing sexually transmitted diseases when used by a user engaging in sexual activities. The apparatus comprises an oral condom mask and two opposite detachable adjustable fasteners.

Figure 1:
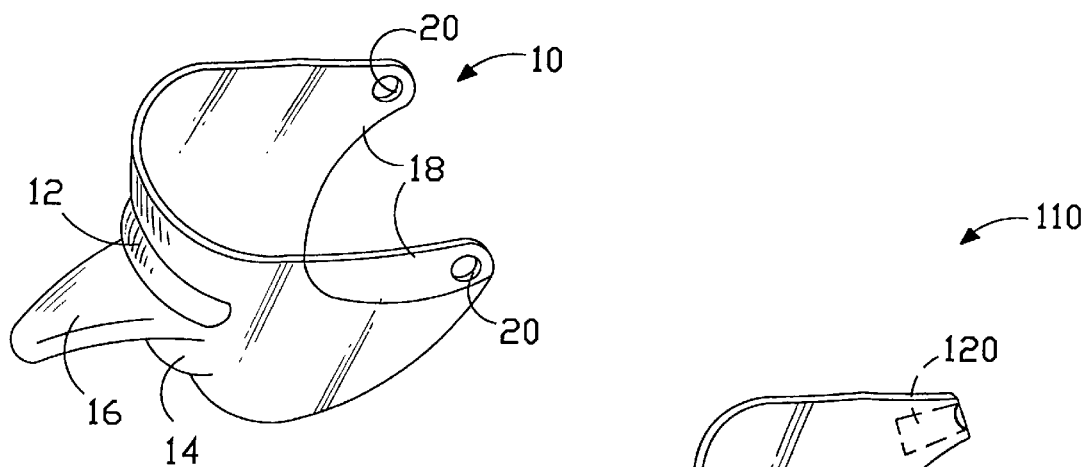
FIG. 1 is an illustrative view of a preferred embodiment of the present invention of a new and improved oral condom mask.

Referring to FIG. 1, there is illustrated a preferred new and improved oral condom mask 10 used in the present invention apparatus for preventing sexually transmitted diseases when used by a user engaging in sexual activities. The oral condom mask 10 used with the present invention is similar in construction disclosed in the '112 Patent. The oral condom mask 10 is generally a thin pliable membrane which is disposable after use. The thin pliable membrane 10 protects all areas of the user's face and extends from approximately beneath the user's nostrils to below the user's chin and jaw, and substantially all of the user's cheeks.

The thin membrane 10 has a conformed shape which has a mouth portion for engaging with the user's lips. The mouth portion has upper lip area 12 and lower lip area 14, which are loose so that they will contour and expand with movement for an unrestricted movement so that the user will experience a natural close feeling when performing oral, vaginal or anal sex using the oral condom mask 10. The thin membrane 10 includes a central tongue portion 16 which is integrally formed and protrudes outwardly away from the membrane when used by the user's tongue. The protruding tongue portion 16 conforms to the user's tongue so that the tongue can be readily and freely moved through the tongue portion 16 of the membrane 10. This provides a natural sensation that the user is not wearing anything at all. The thin membrane 10 further includes two lateral portions 18 which are extended rearwardly toward the user's ears when the user is wearing the oral condom mask 10. Each lateral portion 18 has at least one circular shaped bore 20 therethrough.

Figure 2:
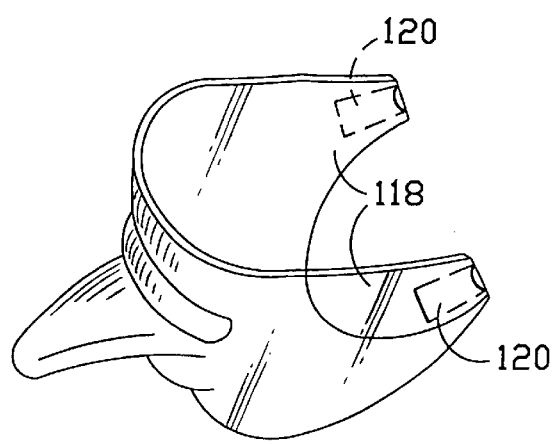
FIG. 2 is an illustrative view of an alternative embodiment of the present invention of a new and improved oral condom mask.

Referring to FIG. 2, there is illustrated an alternative new and improved oral condom mask 110 used in the present invention apparatus. In this embodiment, the oral condom mask 110 is similar in composition and functions the same as previously described above except that the lateral portions 118 each have a hollow lateral cylindrical shaped channel 120 which extends through the end of the lateral portion 118. All other portions of the oral condom mask 110 are the same as previously described above, and the description thereof will not be repeated. Furthermore, the portions of the oral condom mask are numbered correspondingly with 100 added to each number.

Figure 3:
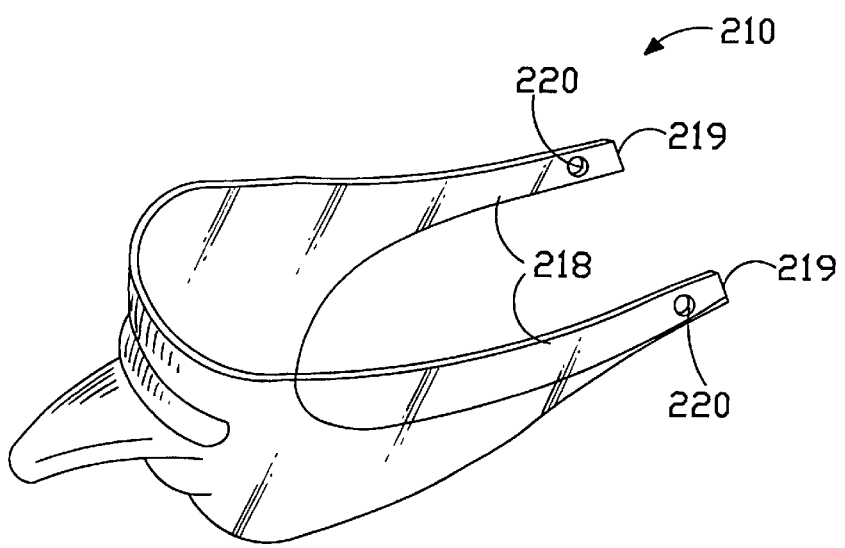
FIG. 3 is an illustrative view of another alternative embodiment of the present invention of a new and improved oral condom mask.

Referring to FIG. 3, there is illustrated another alternative new and improved oral condom mask 210 used in the present invention apparatus. In this embodiment, the oral condom mask 210 is similar in composition and functions the same as previously described in FIG. 1 except that the oral condom mask 210 is provided with elongated lateral portions 218 with lateral ends 219. Each elongated lateral portion 218 has at least one circular shaped bore 220 therethrough and located adjacent to its lateral end 219. All other portions of the oral condom mask 210 are the same as discussed in FIG. 1, and the description thereof will not be repeated. Furthermore, the portions of the oral condom mask are numbered correspondingly with 200 added to each number.

Figure 4:
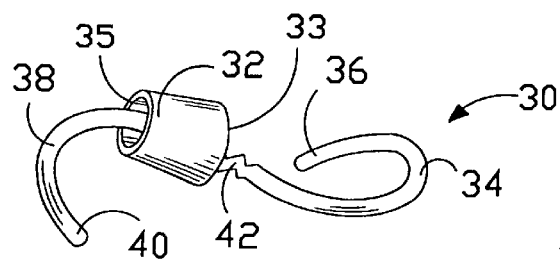
FIG. 4 is a perspective view of a first embodiment of a detachable adjustable fastener used in conjunction with the oral condom mask shown in FIGS. 1 and 2, with a slidable locking sleeve thereon.
Figure 5:
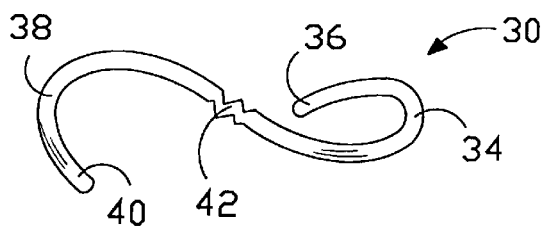
FIG. 5 is a perspective view of the detachable adjustable fastener shown in FIG. 4 without the slidable locking sleeve.

FIG. 4 depicts a perspective view of a first embodiment of a detachable adjustable fastener 30 with a slidable locking sleeve 32. FIG. 5 depicts a perspective view of the detachable adjustable fastener 30 shown in FIG. 4 without the slidable locking sleeve 32. Referring to FIGS. 4 and 5, the detachable adjustable fastener 30 can be used with the oral condom mask shown in FIGS. 1 and 2. In this embodiment, the oral condom mask 10 shown in FIG. 1 will be used to describe the details of the present invention apparatus. The oral condom mask 10 utilizes two identical detachable adjustable fasteners 30, of which only one is shown attached to the oral condom mask in FIG. 10 and of which only one will be described in detail below.

Figure 10:
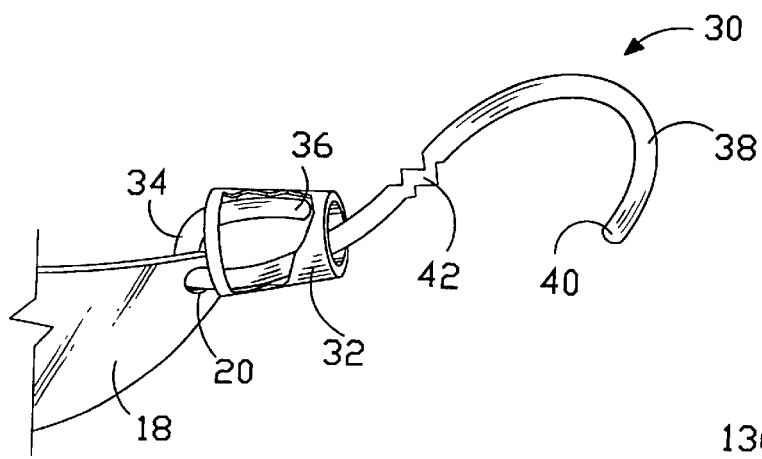
FIG. 10 is an illustrative view of the detachable adjustable fastener shown in FIG. 4 hooked to one of the lateral portions of the oral condom mask shown in FIG. 1, with the slidable locking sleeve in its locked position.

Referring to FIGS. 4, 5 and 10, the detachable adjustable fastener 30 has a front attachment section 34 with an upwardly front hook end 36, a rear engagement section 38 with a downwardly rear hook end 40, and an accordion shaped middle section 42 integrally connected between the front section 34 and the rear section 38. The accordion middle section 42 allows the detachable adjustable fastener 30 to be stretched from a relaxed condition to an expanded condition to extend the length of the fastener 30, where it can fit almost any size head. It will be appreciated that the middle section 42 may include any springy like material integrally connected between the front section 34 and the rear section 38 of the detachable adjustable fastener 30.

Referring to FIGS. 1, 4, 5, and 10, the slidable locking sleeve 32 is generally a hollow cylindrical tapered body which has a widened end 33 and a narrow end 35. The slidable locking sleeve 32 has two positions, a locked position (see FIG. 10) and an unlocked position (see FIG. 4). When the locking sleeve 32 is in the lock position, the widened end 33 allows both the front end 35 and the front section 34 to enter into the hollow tapered body to enclose both the front end 36 and the front section 34 of the fastener 30. The sleeve 32 is slidably moved towards the front section 34 for securing the lateral portion 18 of the thin pliable membrane 10 to the front attachment section 34 of the fastener. The detachable adjustable fastener 30 is installed to the membrane 10 by hooking the front hook end 36 to the bore 20 of the lateral portion 18 of the thin pliable member 10 (see FIG. 10), while the rear hook end 40 is partially hooked over and behind the ear of the user. The detachable adjustable fastener 30 facilitates the wearing of the oral condom mask 10 and can be reusable after oral, vaginal or anal sex.

Figure 6:
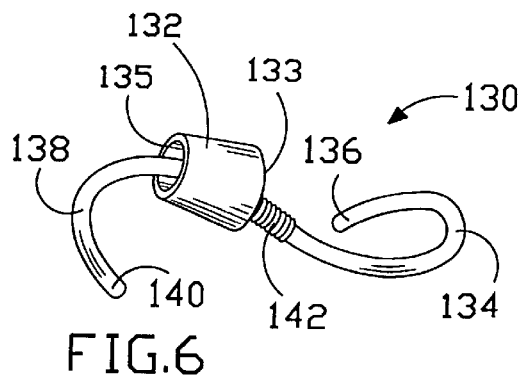
FIG. 6 is a perspective view of a second embodiment of a detachable adjustable fastener used in conjunction with the oral condom mask shown in FIGS. 1 and 2, with a slidable locking sleeve thereon.
Figure 7:
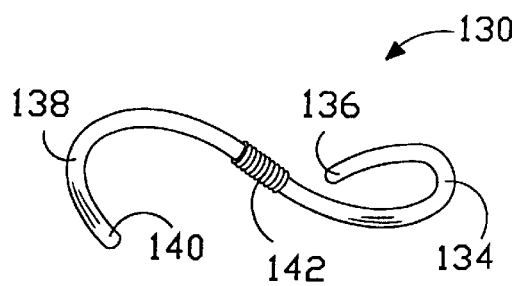
FIG. 7 is a perspective view of the detachable adjustable fastener shown in FIG. 6 without the slidable locking sleeve.

FIG. 6 depicts a perspective view of a second embodiment of a detachable adjustable fastener 130 with a slidable locking sleeve 132. FIG. 7 depicts a perspective view of the detachable adjustable fastener 130 shown in FIG. 6 without the slidable locking sleeve 132. The detachable adjustable fastener 130 can be used with the oral condom mask shown in FIGS. 1 and 2. In this embodiment, the oral condom mask 110 shown in FIG. 2 will be used to describe the details of the present invention apparatus. The oral condom mask 110 utilizes two identical detachable adjustable fasteners 130 of which only one is shown in FIG. 11 and of which only one will be described in detail below.

Figure 11:
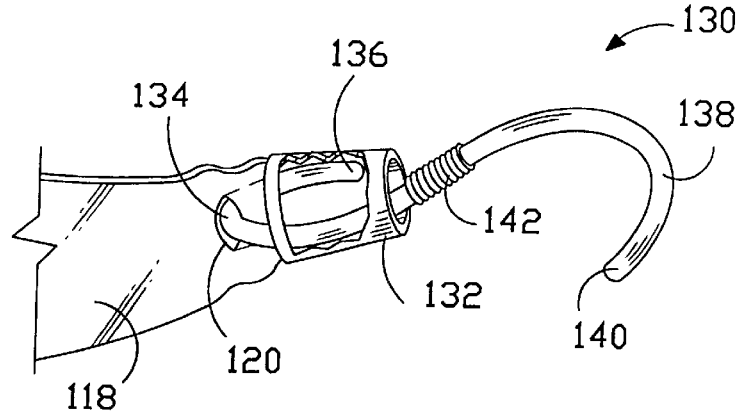
FIG. 11 is an illustrative view of the detachable adjustable fastener shown in FIG. 6 hooked to one of the lateral portions of the oral condom mask shown in FIG. 2, with the slidable locking sleeve in its locked position.

Referring to FIGS. 6, 7 and 11, the detachable adjustable fastener 130 has a front attachment section 134 with an upwardly front hook end 136, a rear engagement section 138 with a downwardly rear hook end 140, and a coil spring or elastic cord middle section 142 integrally connected between the front section 134 and the rear section 138. The front hook end 136 and the rear hook end 140 are located on the same axis. The middle section 142 allows the detachable adjustable fastener 130 to be stretched from a relaxed condition to an expanded condition to extend the length of the fastener 130, where it can fit almost any size head.

Referring to FIGS. 2, 6, 7, and 11, the slidable locking sleeve 132 is generally a hollow cylindrical tapered body which has a widened end 133 and a narrow end 135. The slidable locking sleeve 132 has two positions, a locked position (see FIG. 11) and an unlocked position (see FIG. 6). When the locking sleeve 132 is in the lock position, the widened end 133 allows both the front end 136 and the front section 134 to enter into the hollow tapered body to enclose both the front end 136 and the front section 134 of the fastener 130. The sleeve 132 is slidably moved towards the front section 134 for securing the lateral portion 118 of the thin pliable membrane 110 to the front attachment section 134 of the fastener. The detachable adjustable fastener 130 is installed to the membrane 110 by hooking the front hook end 136 to the lateral channel 120 of the lateral portion 118 of the thin pliable member 110 (see FIG. 11), while the rear hook end 140 is partially hooked over and behind the ear of the user. The detachable adjustable fastener 130 facilitates the wearing of the oral condom mask 110 and can be reusable after oral, vaginal or anal sex.

Figure 8:
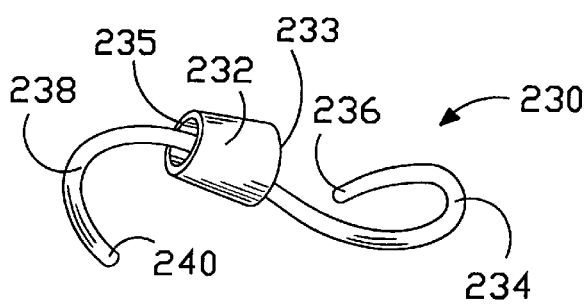
FIG. 8 is a perspective view of a third embodiment of a detachable adjustable fastener used in conjunction with the oral condom mask shown in FIGS. 1, 2 and 3 with a slidable locking sleeve thereon.
Figure 9:
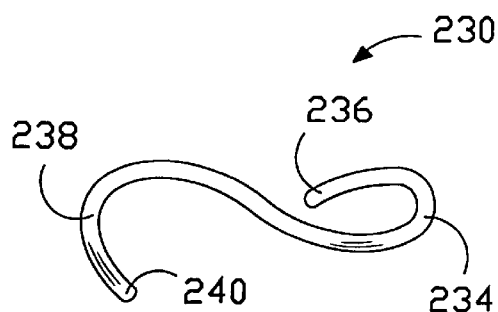
FIG. 9 is a perspective view of the detachable adjustable fastener shown in FIG. 8 without the slidable locking sleeve.
Figure 12:
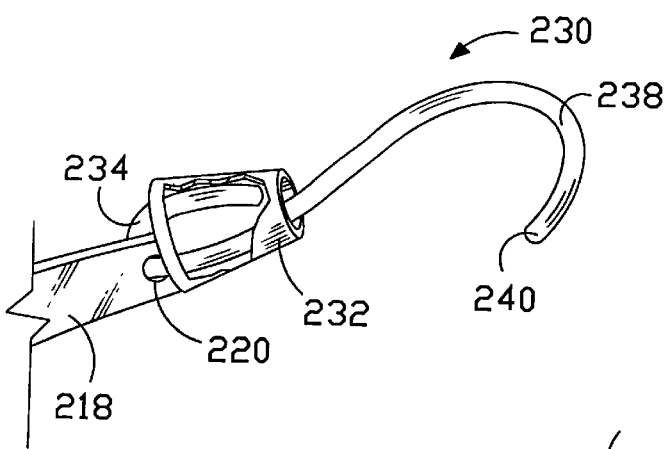
FIG. 12 is an illustrative view of the detachable adjustable fastener shown in FIG. 8 hooked to one of the lateral ends of the oral condom mask shown in FIG. 3, with the slidable locking sleeve in its locked position.

FIG. 8 depicts a perspective view of a third embodiment of a detachable fastener 230 with a slidable locking sleeve 232. FIG. 9 depicts a perspective view of the detachable fastener 230 shown in FIG. 8 without the slidable locking sleeve 232. Referring to FIGS. 8 and 9, the detachable fastener 230 can be used with any one of the oral condom mask shown in FIGS. 1, 2 and 3. In this embodiment, the oral condom mask 210 shown in FIG. 3 will be used to describe the details of the present invention apparatus. In addition, the detachable fastener 230 is not adjustable in the lengthwise direction. The oral condom mask 210 utilizes two identical detachable fasteners 230 of which only one is shown in FIG. 12 and of which only one will be described in detail below. The detachable fastener 230 has a front attachment section 234 with an upward front hook end 236 and a rear engagement section 238 with a downward rear hook end 240. The front hook end 236 and rear hook end 240 are located on the same axis.

Referring to FIGS. 3, 8, 9, and 12, the slidable locking sleeve 232 is generally a hollow cylindrical tapered body which has a widened end 233 and a narrow end 235. The slidable locking sleeve 232 has two positions, a locked position (see FIG. 12) and an unlocked position (see FIG. 8). When the locking sleeve 232 is in the lock position, the widened end 233 allows both the front end 236 and the front section 234 to enter into the hollow tapered body to enclose both the front end 236 and the front section 234 of the fastener 230. The sleeve 232 is slidably moved towards the front section 234 for securing the lateral portion 218 of the thin pliable membrane 210 to the front attachment section 234 of the fastener. The detachable fastener 230 is installed to the membrane 210 by hooking the front hook end 236 to the bore 220 of the lateral portion 218 of the thin pliable member 210 (see FIG. 12), while the rear hook end 240 is partially hooked over and behind the ear of the user. The detachable fastener 230 facilitates the wearing of the oral condom mask 210 and can be reusable after oral, vaginal or anal sex.

Figure 13:
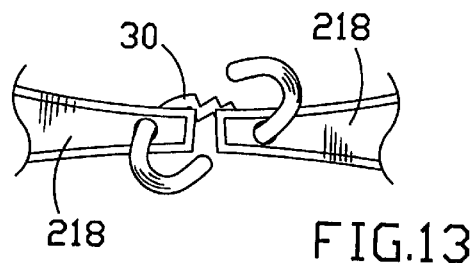
FIG. 13 is an illustrative view of the detachable adjustable fastener shown in FIG. 5 without the slidable locking sleeve, showing an alternative method of attaching the lateral portions of an oral condom mask.

It will be appreciated that the detachable fasteners shown in shown in FIGS. 3, 5, 7 and 9 may be used by physically challenged persons having limited use of the ear in which to adequately engage the fasteners. The physically challenged person can have assess to the use of the oral condom, by using one detachable fastener and having the hook ends respectively hooked to the bores at opposite sides of the oral condom mask, whereby the detachable fastener now becomes a latching mechanism (see FIG. 13). The oral condom mask 210 can be used with any one of the detachable fastener shown in FIGS. 5, 7 and 9. For ease of understanding, the oral condom mask 210 shown in FIG. 3 and the detachable fastener 30 shown in FIG. 5 will be used to describe the details of how the latching mechanism functions.

Referring to FIGS. 3, 5, 7 and 9, the detachable adjustable fastener 30 is installed to the membrane 210 by respectively hooking the hook ends 36 and 40 to one of the bores 220 on each lateral portion 218 of the thin pliable membrane 210, and securing the lateral ends 219 of the thin pliable membrane 210 to the attachment section 34 and the engagement section 38 of the fastener 30. The detachable adjustable fastener 30 facilitates the wearing of the oral condom mask 210 and can be reusable after oral, vaginal or anal sex.

The present invention conforms to conventional forms of manufacture or any other conventional way known to one skilled in the art, and is of simple construction and is easy to use. By way of example, the detachable fasteners may be made of flexible plastic material or any suitable material known to one skilled in the art.

Defined in detail, the present invention is an apparatus for preventing sexually transmitted diseases when used by a user performing oral, vaginal or anal sex, the apparatus comprising: (a) a generally disposable thin pliable membrane conformed to the face and lips of the user such that the thin membrane covers all areas of the face and extending from approximately beneath the nostrils to below the chin and jaw, and covering the cheeks of the user, the thin membrane having a protruding tongue portion extending outwardly for receiving the user's tongue such that the user's tongue can be readily moved, a mouth portion being conformed to the user's lips such that the user's lips can be readily moved, and two opposite lateral portions extending rearwardly toward the user's ears; and (b) two detachable adjustable fasteners each having a front attachment section with an upwardly bending front hook end respectively hooked to respective one of each lateral portion of the thin membrane, a rear engagement section with a downwardly bending rear hook end for respectively partially engaging over and behind a respective one of the user's ears, a springy middle section integrally connecting the front and rear sections and being stretchable from a relaxed condition to an expanded condition to respectively extend the length of each detachable adjustable fastener.

Defined alternatively in detail, the present invention is a detachable fastener used by a user in conjunction with a protective mask, comprising: (a) a membrane being conformed to the user's face and having a protruding portion for receiving the user's tongue, and two lateral portions; and (b) a front section attachable to one end of the membrane, a rear section partially engageable over and behind the user's ear, and a springy middle section connecting the front and rear sections and being stretchable from a relaxed condition to an expanded condition to extend the length of the detachable adjustable fastener; (c) whereby the membrane is adapted to be fixedly retained upon the user's face and the detachable fastener facilitates the wearing of the protective mask.

Defined also alternatively in detail, the present invention is a latching mechanism used by a user in conjunction with a protective mask, comprising: (a) a thin membrane being conformed to the user's face and having a protruding portion for receiving the user's tongue, a mouth portion being conformed to the user's lips, and two elongated lateral portions with lateral ends, each lateral portion having at least one circular shaped bore therethrough; and (b) a detachable adjustable fastener with hook sections attachable at opposite ends of the thin membrane, the hook ends being located at opposite ends of the same axis, and a springy middle section being stretchable from a relaxed condition to an expanded condition to extend the length of the detachable adjustable fastener; (c) whereby the thin membrane is adapted to be fixedly retained upon the user's face and the detachable adjustable fastener facilitates the wearing of the protective mask.

Defined further alternatively in detail, the present invention is an apparatus for preventing sexually transmitted diseases when used by a user performing oral, vaginal or anal sex, the apparatus comprising: (a) a generally disposable thin pliable membrane conformed to the face and lips of the user such that the thin membrane covers all areas of the face and extending from approximately beneath the nostrils to below the chin and jaw, and covers the cheeks of the user, the thin membrane having a protruding tongue portion extending outwardly for receiving the user's tongue such that the user's tongue can be readily moved, a mouth portion being conformed to the user's lips such that the user's lips can be readily moved, and two opposite lateral portions extending rearwardly toward the user's ears; and (b) two detachable fasteners each having a front attachment section and a rear engagement section are located on the same axis, the front hook end respectively attached to one end of the membrane, and the rear hook end with a downwardly bending rear end for respectively partially engaging over and behind a respective one of the user's ears.

Defined broadly, the present invention is a detachable fastener used by a user in conjunction with a protective mask, comprising: (a) a membrane being conformed to the user's face and having a protruding portion for receiving the user's tongue, and two lateral portions; and (b) a front hook end attachable to one end of the protective mask, a rear hook end partially engageable over and behind the user's ear, wherein the front and rear sections are located on the same axis; (c) whereby the membrane is adapted to be fixedly retained upon the user's face and the detachable fastener facilitates the wearing of the protective mask.

Defined alternatively broadly, the present invention is a latching mechanism used by a user in conjunction with a protective mask, comprising: (a) a thin membrane being conformed to the user's face and having a protruding portion for receiving the user's tongue, a mouth portion being conformed to the user's lips, and two elongated lateral portions with lateral ends, each lateral portion having at least one circular shaped bore therethrough; and (b) a detachable fastener with hook end sections attachable at opposite ends of the thin membrane, the hook ends being located at opposite ends of the same axis; (c) whereby the thin membrane is adapted to be fixedly retained upon the user's face and the detachable fastener facilitates the wearing of the protective mask.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

The present invention has been described in considerable detail in order to comply with the patent laws by providing full public disclosure of at least one of its forms. However, such detailed description is not intended in any way to limit the broad features or principles of the present invention, or the scope of the patent to be granted. Therefore, the invention is to be limited only by the scope of the appended claims.

What is claimed is:

1. An apparatus for preventing sexually transmitted diseases when used by a user performing oral, vaginal or anal sex, the apparatus comprising:
    a. a generally disposable thin pliable membrane conformed to the face and lips of said user such that the thin membrane covers all areas of the face and extending from approximately beneath the nostrils to below the chin and jaw, and covering the cheeks of said user, the thin membrane having a protruding tongue portion extending outwardly for receiving the user's tongue such that the user's tongue can be readily moved, a mouth portion being conformed to the user's lips such that the user's lips can be readily moved, and two opposite lateral portions extending rearwardly toward the user's ears; and
    b. two detachable adjustable fasteners each having a front attachment section with an upwardly bending front hook end respectively hooked to respective one of said each lateral portion of said thin membrane, a rear engagement section with a downwardly bending rear hook end for respectively partially engaging over and behind a respective one of the user's ears, a springy middle section integrally connecting the front and rear sections and being stretchable from a relaxed condition to an expanded condition to respectively extend the length of each detachable adjustable fastener.

2. The apparatus in accordance with claim 1 wherein said thin membrane is made of plastic.

3. The apparatus in accordance with claim 1 wherein said each detachable adjustable fastener is made of flexible material.

4. The apparatus in accordance with claim 1 wherein said each detachable adjustable fastener is reusable.

5. The apparatus in accordance with claim 1 wherein said springy middle section of said each detachable adjustable fastener includes an accordion shaped spring.

6. The apparatus in accordance with claim 1 wherein said springy middle section of said each detachable adjustable fastener includes a coil shaped spring.

7. The apparatus in accordance with claim 1 wherein said springy middle section of said each detachable adjustable fastener includes an elastic cord.

8. The apparatus in accordance with claim 1 wherein said each detachable adjustable fastener further comprises a slidable cylindrical shaped sleeve which encloses said front and rear section for respectively securing said each lateral side of said membrane to a respective adjustable fastener.

9. The apparatus in accordance with claim 1 wherein each of said two lateral portions of said membrane further comprises a circular bore therethrough for allowing said front hook end of said each detachable adjustable fastener to be hooked thereto.

10. The apparatus in accordance with claim 1 wherein each of said two lateral portions of said membrane further comprises a lateral channel for allowing said front hook end of said each detachable adjustable fastener to be hooked therein.

11. A detachable fastener used by a user in conjunction with a protective mask, comprising:
   a. a membrane being conformed to the user's face and having a protruding portion for receiving the user's tongue, and two lateral portions; and
   b. a front section attachable to one end of said membrane, a rear section partially engageable over and behind the user's ear, and a springy middle section connecting the front and rear sections and being stretchable from a relaxed condition to an expanded condition to extend the length of the detachable adjustable fastener;
   c. whereby said membrane is adapted to be fixedly retained upon the user's face and said detachable fastener facilitates the wearing of said protective mask.

12. A latching mechanism used by a user in conjunction with a protective mask, comprising:
   a. a thin membrane being conformed to the user's face and having a protruding portion for receiving the user's tongue, a mouth portion being conformed to the user's lips, and two elongated lateral portions with lateral ends, each said lateral portion having at least one circular shaped bore therethrough;
   b. a detachable adjustable fastener with hook sections attachable at opposite ends of said thin membrane, and a springy middle section being stretchable from a relaxed condition to an expanded condition to extend the length of the detachable adjustable fastener;
   c. whereby said thin membrane is adapted to be fixedly retained upon the user's face and said detachable adjustable fastener facilitates the wearing of said protective mask.

13. An apparatus for preventing sexually transmitted diseases when used by a user performing oral, vaginal or anal sex, the apparatus comprising:
   a. a generally disposable thin pliable membrane conformed to the face and lips of said user such that the thin membrane covers all areas of the face and extending from approximately beneath the nostrils to below the chin and jaw, and covers the cheeks of said user, the thin membrane having a protruding tongue portion extending outwardly for receiving the user's tongue such that the user's tongue can be readily moved, a mouth portion being conformed to the user's lips such that the user's lips can be readily moved, and two opposite lateral portions extending rearwardly toward the user's ears;
   b. two detachable fasteners each having a front attachment section and a rear engagement section, a front hook end respectively attached to one end of said membrane, and a rear hook end with a downwardly bending rear end for respectively partially engaging over and behind a respective one of the user's ears; and
   c. said each detachable fastener further comprises a slidable cylindrical shaped sleeve enclosing said front and rear section for respectively securing said each lateral side of said membrane to a respective fastener.

14. The apparatus in accordance with claim 13 wherein said each detachable fastener is made of flexible material.

15. The apparatus in accordance with claim 13 wherein said each detachable fastener is reusable.

16. The apparatus in accordance with claim 13 wherein each of said two lateral portions of said membrane further comprises a circular bore therethrough for allowing said front hook end of said each detachable fastener to be hooked thereto.

17. The apparatus in accordance with claim 13 wherein each of said two lateral portions of said membrane further comprises a lateral channel for allowing said front hook end of said each detachable fastener to be hooked therein.

\* \* \* \* \*